(12) United States Patent
Sadeghi et al.

(10) Patent No.: US 7,255,813 B2
(45) Date of Patent: Aug. 14, 2007

(54) NADH/NADPH-CONTAINING COMPOUND

(75) Inventors: Behzad Sadeghi, Vienna (AT); Peter Kössler, Mariapfarr (AT); Norbert Fuchs, Mariapfarr (AT)

(73) Assignee: Nutropia Ernahrungsmedizinische Forschungs GmbH, Unternberg (AT)

( * ) Notice: Subject to any disclaimer, the term of this patent is extended or adjusted under 35 U.S.C. 154(b) by 0 days.

(21) Appl. No.: 10/535,330

(22) PCT Filed: Nov. 19, 2003

(86) PCT No.: PCT/AT03/00346

§ 371 (c)(1),
(2), (4) Date: May 18, 2005

(87) PCT Pub. No.: WO2004/045626

PCT Pub. Date: Jun. 3, 2004

(65) Prior Publication Data

US 2006/0011891 A1 Jan. 19, 2006

(30) Foreign Application Priority Data

Nov. 19, 2002 (AT) .............................. A 1734/2002

(51) Int. Cl.
*C09K 15/32* (2006.01)
*C09K 15/18* (2006.01)
*C09K 15/22* (2006.01)

(52) U.S. Cl. ............ 252/400.61; 252/399; 252/400.21; 252/400.22; 252/400.23; 252/400.24; 252/400.62; 252/401

(58) Field of Classification Search ............ 252/400.61
See application file for complete search history.

(56) References Cited

U.S. PATENT DOCUMENTS

| 3,934,369 | A | * | 1/1976 | Rebeiz ........................ 435/118 |
| 5,332,727 | A | * | 7/1994 | Birkmayer ................... 514/52 |
| 5,760,206 | A | * | 6/1998 | Hitz et al. ................... 536/23.6 |
| 5,777,190 | A | * | 7/1998 | Shah et al. .................. 435/128 |
| 5,952,312 | A | * | 9/1999 | Birkmayer ................... 514/47 |
| 6,124,242 | A | * | 9/2000 | Wagner et al. .............. 504/170 |
| 6,133,227 | A | * | 10/2000 | Barnabas et al. ........... 510/530 |

FOREIGN PATENT DOCUMENTS

| EP | 1 161 884 A1 | * 12/2001 |
| JP | 59 216824 | 12/1984 |
| JP | 60 132987 | 7/1985 |
| JP | 11 292737 | 10/1999 |
| RU | 2 143 212 | 12/1999 |

* cited by examiner

*Primary Examiner*—Joseph D. Anthony
(74) *Attorney, Agent, or Firm*—Fulbright & Jaworski L.L.P.

(57) ABSTRACT

The invention relates to a compound containing at least one health promoting isolated antioxidant A having a redox potential of less than 180 mV and at least one stabilising antioxidant B which has a standard redox potential which is less than the standard redox potential of the antioxidant A. The use of the inventive compound and method for the production thereof are also disclosed.

10 Claims, 1 Drawing Sheet

NADH/NADPH-CONTAINING COMPOUND

Figure 1:
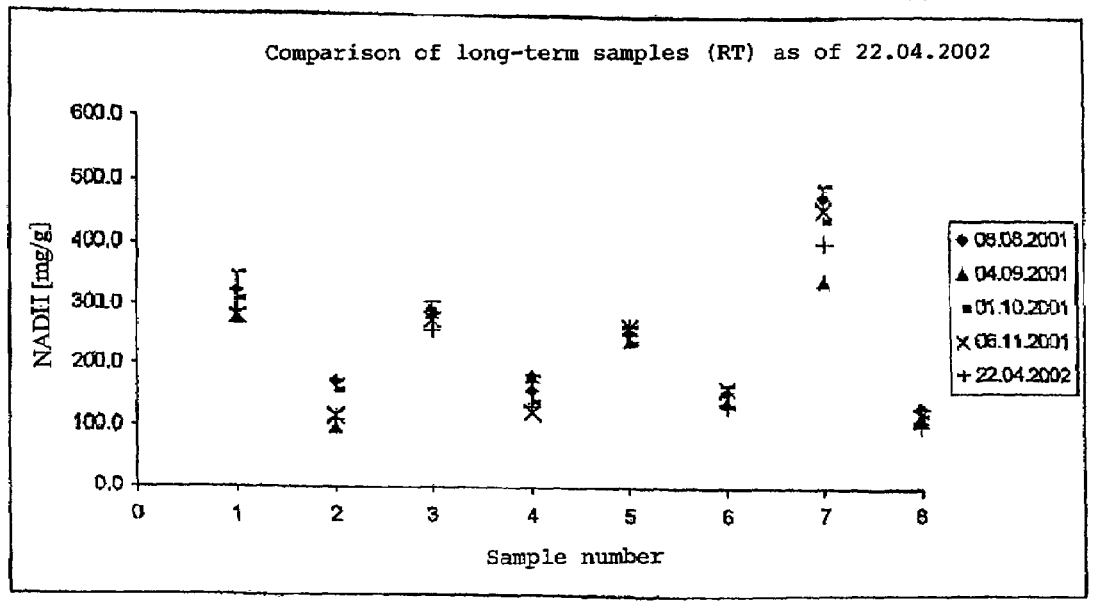

This application is a national phase application under 35 U.S.C. § 371 of International Application No. PCT/AT2003/000346 filed 19 Nov. 2003, which claims priority to Austrian Application No. A 1734/2002 filed 19 Nov. 2002. The entire text of each of the above-referenced disclosures is specifically incorporated herein by reference without disclaimer.

The present invention relates to a composition as well as a method for its preparation and the use of said composition.

Being a heterotrophic creature, man needs macromolecules (protein, fats, carbohydrates) every day in order meet his/her energetic and substantial demands. In the context of the energy metabolism, human cells burn macronutrient cleavage products by transferring electrons of these cleavage products to the molecular respiratory oxygen. In doing so, thermal energy and biochemical storage energy are formed as depots in the form of ATP and other phosphates rich in energy. The major portion of these cleavage products is, however, also used for the biosynthesis and regeneration of new biological structures (e.g., enzymes, hormones, body cells, connective tissue substance). Those synthetic procedures too require both electrons and biochemical energy (e.g., ATP) released from combustion processes. Both oxidation (which releases energy by destroying chemical structures) and reduction (which builds up new biological structures by energy consumption) are metabolic processes by which electrons are transferred from macronutrient molecules. Thus, all metabolic processes occurring in the human body are oxidation and reduction processes, so-called redox processes, for which "health-promoting" antioxidants are essential.

Since electrons cannot be transferred in isolated states during biochemical processes, the cell requires transfer molecules, which are also referred to as electron carriers. In principle, every atom, every molecule, which transfers electrons to a reaction partner, is an electron carrier or—in relation to that partner onto which the electron is transferred—an electron donor, or a reductant, or an antioxidant, respectively. The potential of transferring electrons varies from one molecule to another. The standard redox potential is the lower the stronger the electron pressure exerted by that molecule, and the higher the lower said electron pressure. Molecules having low standard redox potentials carry electrons rich in energy, which flow either into biochemical energy or into the synthesis of new biological structures of high order, which means that the vitality of the human body depends, in the end, on the height of the portion of energy-rich electrons in food. NADH, for instance, ranks among the most important and energy-richest electron carriers of human metabolism because of its extremely low standard redox potential of −320 mV. NADH transfers electrons (as bound "hydride") to the molecular respiratory oxygen primarily for the purpose of recovering energy (while simultaneously forming ATP). That reaction course—which is referred to as oxidative phosphorylation or respiratory chain—takes place in the mitochondrias of the cells. Thus, NADH is, so to speak, the symbol of cellular energy.

NADH promotes cognitive, intellectual and motoric abilities in Parkinson's disease and Alzheimer' disease as well as in the event of fatigue, lethargy and chronic fatigue syndrome. NADH also enhances vitality and motivation, sometimes NADH is also reported to eliminate libido and potency disorders. Depressions, weaknesses of learning and concentration may be due to limited endogenous NADH synthesis just as reduced physical abilities under physical strain and in serious sports. Last but not least, NADH promotes the synthetic and detoxicating functions of the liver.

There are, however, a number of other such "health-promoting" antioxidants which are largely produced in the organism itself. In principle, the human organism is, thus, able to build up these antioxidants like, e.g., NADH, by itself. NADH is enzymatically formed, via several metabolic steps and at a high energy consumption, from niacin, or its precursor L-tryptophan, and from the phosphorus-containing sugar 5-phosphoribosyl-1-pyrophosphate (PRPP), a ribose containing three phosphate residues. To the thus formed nicotinate ribonucleotide is transferred a molecule residue from ATP (namely AMP). The final synthesis step comprises the transfer of a glutamin amino group, resulting in $NAD^+$. If a further phosphate (from ATP) is linked to those molecules, (the "regeneration molecule") NADP will result therefrom. The biological activation proper, of $NAD^+$—by the transfer of a hydride from nutrient molecules—likewise takes place by ATP degradation, i.e. at a high energy consumption. Niacin and glutamine will, thus, promote the endogenous synthesis of NADH provided the cellular pool of ATP and energy-rich synthesis enzymes is sufficiently filled.

In principle, it would, however, also be feasible to supply the desired antioxidants, which are essential to the health of an organism, exogenously through food. Due to their very low standard redox potential, these antioxidants are, however, extremely sensitive to oxygen and, therefore, practically unavailable in reduced form.

The object of the present invention, therefore, resides in providing health-promoting antioxidants having low redox potentials of below −180 mV in storage-stable form to also enable the exogenous intake of said antioxidants in addition to their endogenous production. To this end, the storage stability is to be so high as to provide protection to said antioxidants against oxidative and chemical decomposition over a period of at least 6 months.

In accordance with the invention, this object is achieved by a composition which is characterized in that it comprises at least one isolated, health-promoting antioxidant A having a redox potential of below −180 mV and at least one isolated antioxidant B stabilizing said antioxidant A and having a standard redox potential ranging below the standard redox potential of said antioxidant A.

By providing an antioxidant B having a lower standard redox potential than the antioxidant A, it was surprisingly found that the antioxidant A, unlike conventional compositions, unlike conventional compositions remains sufficiently storage-stable and protected against decomposition:

EP 1 161 884 A1, for instance, discloses that a food additive comprising NADH is stabilized by vitamin E. Yet, vitamin E has a higher standard redox potential than the antioxidant B according to the invention; tocopherol, for instance, has a standard redox potential of +300 mV.

U.S. Pat. Nos. 5,332,727 and 5,952,312 relate to a composition comprising NADH and NADPH, respectively, and $NaHCO_3$, ascorbic acid, sodium ascorbate, tocopherol, tocopherol acetate or polyvinylpyrrolidone as stabilizers. Yet, those stabilizers too have standard redox potentials higher than that of the antioxidant B according to the invention, and they are not apt to optimally stabilize, for instance, NADH or NADPH via a reduced standard redox potential. Ascorbic acid, for instance, has a redox potential of +80 mV.

The antioxidants provided in the composition may be both of synthetic and of natural origin, wherein it is essential that the antioxidants are provided in isolated, i.e., purified form, wherein it is feasible, as already pointed out above, to provide a single, isolated antioxidant or a mixture of isolated antioxidants with at least one of said antioxidants B having a standard redox potential lower than that of the antioxidant A to be protected. By "isolated", it is understood that the purified antioxidant is present in the composition at a concentration higher than that of natural mixtures, i.e., mixtures occurring in nature. Such concentrations preferably exceed 20% and, preferably, 40% and, still more preferably, 60% of the composition, excluding stabilizers, salts and other auxiliary substances. The redox potential of the antioxidant B may, for instance, be below −190 mV, below −320 mV or below −600 mV.

The term "antioxidant A" is to denote health-promoting antioxidants having redox potentials of below −180 mV, the term "health-promoting" meaning that the antioxidant is important for the functioning of a human or animal organism. Preferably, those antioxidants are encompassed, which are already produced in the human or animal organism, yet are endogenously produced in the body itself in too low a concentration on account of congenital diseases or external influences, such that an exogenous supply is essential to providing optimum health. Antioxidants A of this kind include NADH, NADPH, $FADH_2$, $FMNH_2$, FADH, FMNH etc.

In the context of the present application, the term "antioxidant B" serves to denote an antioxidant having a lower standard redox potential than the antioxidant A present in the composition, such that the antioxidant A will be stabilized by the antioxidant B. In doing so, said antioxidant will, above all, not exert any direct influence on the health of the human or animal organism.

If only one antioxidant A, for instance FADH, is present in the composition, having a standard redox potential of −190 mV, one antioxidant B having a standard redox potential of below −190 mV will do in the composition in order to stabilize FADH via the redox potential. If, on the other hand, a second or several other antioxidants A having lower redox potentials, such as, e.g., $FADH_2$ (−220 mV) and/or $FMNH_2$ (−220 mV), are present in the composition besides FADH, at least one antioxidant B having a standard redox potential of below −220 mV will have to be present in the composition. It goes without saying that an antioxidant B having a redox potential of below −190 mV may be additionally present. Whether one or several antioxidants B are contained in the composition will have to be decided from one case to another as a function of the application options implied by the manufacturing process, cost reasons and other factors. What is essential in any event is that for the stabilization of the antioxidant A having the lowest redox potential an antioxidant B having an even lower redox potential will always be present.

The difference between the antioxidant A and the antioxidant B resides in that the antioxidant A has a health-promoting effect, while the antioxidant B not necessarily, but in the first place serves to stabilize the antioxidant A.

It is of particular advantage if the antioxidant A is selected from the group consisting of NADH, NADPH, reduced alpha-liponic acid, reduced glutathione, $FADH_2$, $FMNH_2$, FADH and/or FM-NH. These antioxidants have the following redox potentials:

Reduced alpha-liponic acid: −290 mV, glutathione: −230 mV, $FADH_2$: −220 mV, $FMNH_2$: −220 mV, FADH: −190 mV, FMNH: −190 mV and NADH: −320 mV. These antioxidants are of particular importance to the health of human and animal organisms and possess standard redox potentials of below −180 mV. These substances are extremely sensitive, and it is therefore difficult to make these substances available in storage-stable form without the antioxidants changing, e.g., chemically and without having to admix unhealthy preservatives. It goes without saying that all of these antioxidants may also be present together in the composition. In that case, it is only important that a sufficient amount of antioxidant B will be present in order to stabilize all antioxidants A.

The composition may be provided in any form suitable for processing, for instance, in the form of conventional foods, nutritional supplements, dietetic foods, drugs, etc.

The antioxidant B is preferably a chlorophyll and/or a reduced ferredoxin. It turned out in a surprising manner that chlorophyll is particularly suitable as a protection means against the decomposition of antioxidants having redox potentials of below −180 mV, wherein it is feasible to provide just a single or even several type(s) of chlorophyll, for instance, chlorophyll A, B, C and/or D, photosystem I chlorophylls having lower redox potentials than photosystem II chlorophylls.

In a particularly preferred manner, the composition additionally comprises an oxygen-sequestering substance. If an oxygen-sequestering substance is provided in the composition in addition to the antioxidant B, any contact of the antioxidant A with oxygen, and hence an oxidation process of the antioxidant A, will be prevented. Even in this case it is, of course, feasible to provide not only one, but two or several different oxygen-sequestering substances in the composition, the term "oxygen-sequestering substance" encompassing any substance or substance composition which reduces, or largely prevents, any contact between the antioxidant A and oxygen.

Preferably, said oxygen-sequestering substance is an oil-containing substance. Oil-containing substances are especially suitable as oxygen-sequestering agents of the composition according to the invention, because they effectively prevent, or at least strongly reduce, any contacting between oxygen and the antioxidant A of the composition and, furthermore, also because a number of oil-containing substances with health-promoting properties are known. Again, it is, of course, also feasible to use not only one oil-containing substance, but different oil-containing substances, for instance, oils containing several un-saturated fatty acids or oils of different origins.

In this context, it is particularly suitable if the oxygen-sequestering substance is an oil-containing substance comprising at least one further antioxidant C. This provides additional protection to the antioxidant A, since the oxidative decomposition of the antioxidant A will not only be prevented by the antioxidant B, but, in a double manner, also by the oil-containing substance, firstly because the contact between the antioxidant A and oxygen is prevented or largely reduced and secondly, in the presence of oxygen, because the latter is already reduced by the antioxidant C contained in the oily substance.

In particularly preferred manner, the oxygen-sequestering substance comprises vitamin E and, in particular, tocotrienol as said antioxidant C. Vitamin E is an antioxidant that offers additional health-promoting properties such as, for instance, cholesterol-lowering and cell-protecting properties. In this respect, it is feasible to provide one type of vitamin E, for instance a tocopherol type, or at least two or more types of vitamin E. In doing so, it is, however, particularly beneficial if tocotrienol is provided, because tocotrienol has an antioxidative potential that is 50 to 1000 times higher than that of synthetic tocopherols. Being lipophilic antioxidants, tocotrienols play an important biological role in the context of the antioxidative protection of nuclei (genetic material), mitochondrias (cellular energy supply), the endoplasmatic reticulum (cellular synthetis output) as well as on the cell membrane (stability and life of tissues). The fields of application of tocotrienols in nutritional medicine, for instance, comprise the immune system, the cardiovascular system, the muscle/tendon/joint complex, the liver as the detoxicating organ, the skin as well as regenerative processes of the nervous system. It goes without saying that both tocotrienols and tocopherols may be provided in the oxygen-sequestering substance.

A particularly favorable composition is made available in that said antioxidant A and said antioxidant B are provided at a ratio of between 10:1 and 1:10, preferably 3:1 and 1:3.

It has been shown that these ratios are the optimum ratios for protecting the antioxidant A, a ratio of, in particular, 1:1 to 1:3 providing comprehensive protection to the antioxidant A.

In a preferred manner, the composition further comprises one or several auxiliary agents. Depending on the type of application of the composition, said auxiliary agents include pharmaceutically acceptable carriers, emulsifiers, stabilizers, coloring agents, flavoring agents, additional pharmaceutical agents, food technological auxiliary agents and the like. Silica, for instance, is particularly suitable as a carrier, because it is neutral and has no effect on the redox potentials of the ingredients.

Another aspect of the present invention relates to the use of the above-described composition according to the invention as a nutritional supplement. In this manner, the antioxidant A can simply be taken as a nutritional supplement without suffering from any disorder and having medical treatment, such as, e.g., in the event of fatigue, which afflicts many people especially in spring. Yet, even with elevated performances, such as intensive sport activities, under examination stress etc., the composition can be taken in the form of a nutritional supplement. To this end, the composition is provided in conventional forms of nutritional supplements, foods, or dietetic foods.

A further aspect of the present invention relates to the use of the above-defined composition according to the invention as a drug. Since the ingestion of the antioxidant A also exerts a positive influence particularly in the event of diseases like chronic fatigue syndrome, depressions or motoric weaknesses, it is favorable to provide the composition according to the invention in the form of a drug, with common drug forms being provided in this case too.

A further aspect of the present invention relates to the use of an above-described composition according to the present invention for preparing an agent selected from the group consisting of an agent promoting oxidative phosphorylation, an agent promoting cognitive, intellectual and/or motoric abilities, an agent promoting the synthesis and detoxication functions of the liver, an agent for treating fatigue, lethargy, libido and potency disorders, depressions, weaknesses of learning and concentration.

It has been shown in a surprising manner that the composition according to the invention is particularly effective in those fields of applications.

It is, moreover, beneficial if the composition is provided in the form of tablets, a liquid, capsules, coated tablets, a syrup, a lotion, a cream or a powder.

Depending on the field of use, the one or the other form will be more suitable, thus tablets, capsules and coated tablets or syrups are, for instance, apt as nutritional supplements. If the composition is to act through the skin or on the skin, a lotion or cream will be particularly suitable. The skilled artisan may choose the necessary auxiliary substances for the respective form.

Another aspect of the present invention relates to a method for preparing a composition according to the invention as described above, wherein the antioxidant A, the antioxidant B as well as, optionally, an oxygen-sequestering substance are mixed with one another, and the composition is optionally processed into tablets, a liquid, capsules, coated tablets, a syrup, a lotion, a cream or a powder.

The mixing step may, for instance, be carried out automatically or manually, in a mixing drum or in any vessel. Further processing is effected according to methods known per se. The advantage of the method according to the invention resides in the fact that no additional measures need be taken to protect the antioxidant A, since protection is already provided by the antioxidant B.

It is particularly favorable if the antioxidant A, the antioxidant oxidant B and optionally the oxygen-sequestering substance are mixed under inert gas. Such an inert gas is, for instance, nitrogen, whereby the access of oxygen to the composition is additionally inhibited or lowered. Thus, the risk of oxidation of the antioxidant A is further reduced.

It is, furthermore, favorable if the composition is processed under inert gas. In this case too, the inert gas may, for instance, be nitrogen, wherein it is particularly beneficial if both the step of mixing and the step of processing to tablets, liquids, capsules, coated tablets, syrups, lotions, creams or powders are carried out under inert gas such that all steps will take place in a manner preventing or reducing the access of oxygen.

Figure 2:
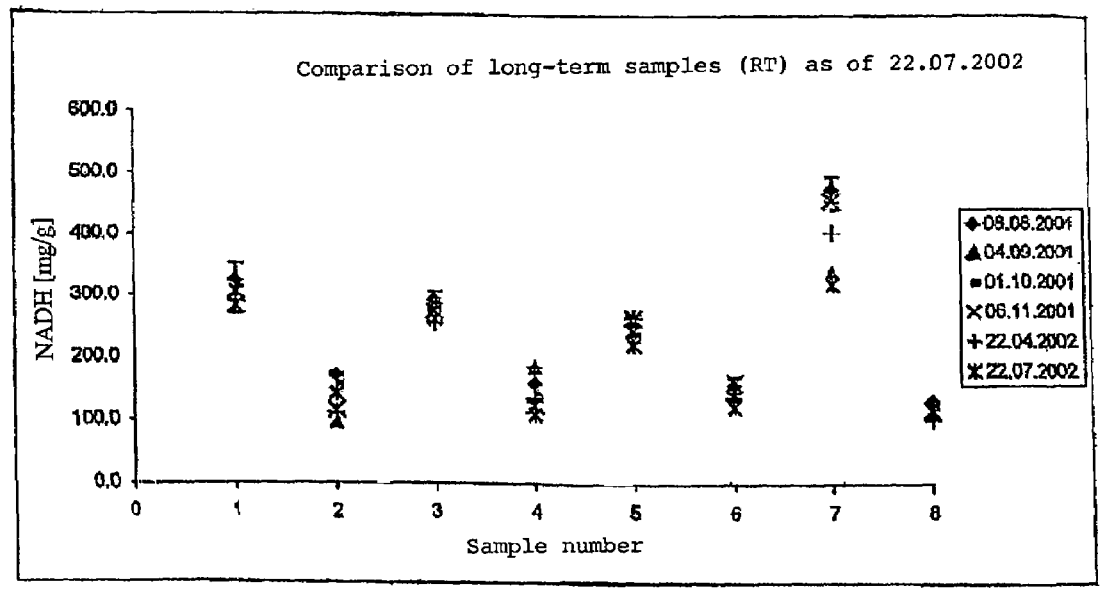

The present invention will now be explained in more detail by way of the following examples and the accompanying Figures, to which it is, however, not to be limited, FIGS. 1 and 2 comparatively illustrating the storage stabilities of different compositions.

EXAMPLE 1

Preparation of Various Compositions

In this example, NADH (−320 mV) was used as antioxidant A. In order to objectivize the NADH-protective action by oxygen-sequestering oils, or by strong antioxidants, mixtures of NADH with a wheat seed oil rich in tocotrienol (in the following referred to as oil) and chlorophyll as antioxidant B having a redox potential of −660 mV were prepared using inert Aerosil as auxiliary substance.

| | |
|---|---|
| Formulation No. 1: | NADH 20 mg |
| | oil 20 mg |
| | Aerosil 20 mg |
| Formulation No. 2: | NADH 20 mg |
| | oil 60 mg |
| | Aerosil 30 mg |
| Formulation No. 3: | NADH 20 mg |
| | chlorophyll 20 mg |
| | Aerosil 20 mg |
| Formulation No. 4: | NADH 20 mg |
| | chlorophyll 80 mg |
| | Aerosil 20 mg |
| Formulation No. 5: | NADH 20 mg |
| | oil 20 mg |
| | chlorophyll 20 mg |
| | Aerosil 20 mg |
| Formulation No. 6: | NADH 20 mg |
| | oil 20 mg |
| | chlorophyll 60 mg |
| | Aerosil 20 mg |

-continued

| | |
|---|---|
| Formulation No. 7: | NADH 20 mg |
| | Aerosil 20 mg |
| Formulation No. 8: | NADH 20 mg |
| | oil 20 mg |
| | chlorophyll 60 mg |
| | Aerosil 20 mg |

Formulations Nos. 1 to 7 were mixed under nitrogen as inert gas, subsequently filled into hard gelatin capsules and packed into polypropylene containers.

Formulation No. 8 was mixed without oxygen as inert gas, subsequently encapsulated—likewise without nitrogen protection—and filled into polypropylene containers.

EXAMPLE 2

Testing of the Storage Stability of the Individual Compositions

All of the 8 test specimens were stored under long-term conditions at 25° C. and 60% relative humidity over a period of six months and chemically/analytically examined in one-month intervals. The analysis was aimed to determine the oxidative decomposition of NADH to $NAD^+$ or other compounds.

The analytical operations were carried out under the following conditions:

Analytical Parameters

| | |
|---|---|
| HPLC: | Agilent 1100 Series with quaternary pump, auto-sampler, column thermostatization and variable wavelength detector (VWD) or fluorescence detector (FLD), respectively |
| Separation column: | LiChrospher ® 100 RP-18 (5 µm) 250 × 4 mm incl. Guard column 4 × 4 mm |
| Column thermostat: | 25° C. |
| Eluant: | Mixture of 900 ml $H_2O$, 60 ml $CH_3CN$, 23 ml THF, 1 ml phosphoric acid and 1.2 g sodium octane sulfonate (NaOSS) |
| Flow rate: | 1.5 ml/min |
| Detection: | VWD: 260 nm |
| | FLD: excitation: 290 nm, emission: 395 nm |
| Retention times: | NADH: 1.04 min |
| | $NAD^+$: 1.34 min |

Standardization

By the aid of dilution series of stock solutions of commercially available NADH (Pfannenschmidt GmbH) and $NAD^+$ (Sigma Aldrich), respectively, straight calibration lines could be determined for the two substances in the ranges of 1-50 mg/l (FLD) and 10-200 mg/l (VWD), respectively.

For the analyses of the formulations, VWD is used because of the concentrations, at lower quantities detection would also be feasible by means of FLD.

Analysis Implementation

The content of a capsule is dosed into a screw-cap bottle, supplemented with 50 ml distilled $H_2O$ and vigorously shaken for one minute.

Suspended matter is filtered off through a spray filter (Sartorius Minisart RC 25, 0.45 µm), and the solution is filled into a vial, whereupon the concentrations of NADH and $NAD^+$ are determined by HPLC/VWD according to the method of external standards.

Results:

The evaluations of the NADH contents of samples Nos. 1 to 8 are indicated in the Table and in the Figures.

TABLE

| Sample number | 8.8.2001 NADH [mg/g] | 8.8.2001 Stand. deviation | 04.09.RT NADH [mg/g] | 01.10.RT NADH [mg/g] | 6.11.RT NADH [mg/g] | 22.04.02RT NADH [mg/g] | 22.7.02RT NADH [mg/g] |
|---|---|---|---|---|---|---|---|
| 1 | 323.1 | 27.2 | 277.0 | 311.6 | 282.1 | 288.9 | 304.5 |
| 2 | 171.7 | 1.9 | 96.8 | 156.7 | 115.6 | 109.8 | 141.7 |
| 3 | 293.7 | 11.8 | 286.3 | 287.7 | 275.0 | 255.7 | 261.8 |
| 4 | 159.5 | 24.4 | 184.4 | 141.7 | 124.4 | 131.6 | 109.2 |
| 5 | 252.8 | 16.3 | 243.4 | 238.8 | 264.7 | 264.8 | 220.9 |
| 6 | 157.4 | 11.9 | 140.7 | 136.6 | 161.5 | 134.7 | 122.6 |
| 7 | 475.3 | 20.2 | 339.1 | 440.8 | 456.2 | 402.8 | 318.8 |
| 8 | 130.1 | 1.2 | 113.1 | 117.7 | 116.8 | 101.7 | 114.9 |

As is apparent from these evaluations, NADH is chemically instable without addition of protective substances because of its oxidation sensitiveness (sample No. 7).

The oxidative degradation of NADH in sample No. 1 and sample No. 2 demonstrates that shielding from oxygen by oily solutions (even if they contain tocotrienols) does have some protective effect, yet is not able to completely prevent the oxidative (albeit retarded) decomposition of NADH over time.

By contrast, the addition of chlorophyll, which has an extremely low redox potential of −600 mV and is thus apparently able to prevent the oxidation of NADH (−320 mV) by, e.g., oxygen from the air has turned out to be optimal (sample No. 3). The combination of chlorophyll and tocotrienol-rich oil also turned out to be highly advantageous, as demonstrated by samples Nos. 5 and 6. From the values of sample No. 8, it is apparent that the antioxidative protection of chlorophyll and tocotrienol-rich oils is apparently so high as to enable the further processing of appropriate mixtures to capsules, tablets or other drug forms even without any inert-gas protection.

The invention claimed is:

1. A composition comprising:
   at least one antioxidant A having a redox potential of below −180 mV, the antioxidant A further defined as NADH or NADPH; and
   at least one antioxidant B that stabilizes antioxidant A and has a standard redox potential below the standard redox potential of antioxidant A, the antioxidant B further defined as an isolated chlorophyll.

2. The composition of claim 1, further comprising an oxygen-sequestering substance.

3. The composition of claim 2, wherein the oxygen-sequestering substance comprise an oil-containing substance.

4. The composition of claim 3, wherein the oil-containing substance comprises at least one further antioxidant C.

5. The composition of claim 4, wherein the antioxidant C comprises vitamin B.

6. The composition of claim 5, wherein the antioxidant C comprises tocotrienol.

7. The composition of claim 1, wherein antioxidant A and antioxidant B are in a ratio of between 10:1 and 1:10.

8. The composition of claim 1, wherein antioxidant A and antioxidant B are in a ratio of between 3:1 and 1:3.

9. The composition of claim 1, wherein antioxidant A is further defined as NADH.

10. The composition of claim 1, wherein antioxidant A is further defined as NADPH.

* * * * *

UNITED STATES PATENT AND TRADEMARK OFFICE
CERTIFICATE OF CORRECTION

| | | |
|---|---|---|
| PATENT NO. | : 7,255,813 B2 | Page 1 of 1 |
| APPLICATION NO. | : 10/535330 | |
| DATED | : August 14, 2007 | |
| INVENTOR(S) | : Behzad Sadeghi et al. | |

It is certified that error appears in the above-identified patent and that said Letters Patent is hereby corrected as shown below:

In claim 5, column 9, line 7, delete "B" and insert --E-- therefor.

Signed and Sealed this

Twenty-seventh Day of November, 2007

JON W. DUDAS
*Director of the United States Patent and Trademark Office*